US011219447B2

(12) United States Patent
Juan et al.

(10) Patent No.: US 11,219,447 B2
(45) Date of Patent: Jan. 11, 2022

(54) SYSTEM AND METHOD FOR SUTURE TRIMMING

(71) Applicant: Terumo Medical Corporation, Somerset, NJ (US)

(72) Inventors: Chun-Chia Juan, Taipei (TW); Rung-Jian Chen, Taipei (TW); Roberto Silva-Torres, Foster City, CA (US)

(73) Assignee: Terumo Medical Corporation, Somerset, NJ (US)

( * ) Notice: Subject to any disclaimer, the term of this patent is extended or adjusted under 35 U.S.C. 154(b) by 158 days.

(21) Appl. No.: 16/331,841

(22) PCT Filed: Sep. 8, 2017

(86) PCT No.: PCT/US2017/050647
§ 371 (c)(1),
(2) Date: Mar. 8, 2019

(87) PCT Pub. No.: WO2018/049138
PCT Pub. Date: Mar. 15, 2018

(65) Prior Publication Data
US 2019/0374215 A1    Dec. 12, 2019

Related U.S. Application Data

(60) Provisional application No. 62/385,436, filed on Sep. 9, 2016.

(51) Int. Cl.
*A61B 17/04*    (2006.01)
*A61B 17/06*    (2006.01)

(52) U.S. Cl.
CPC ...... *A61B 17/0467* (2013.01); *A61B 17/0469* (2013.01); *A61B 17/0485* (2013.01);
(Continued)

(58) Field of Classification Search
CPC ............ A61B 17/0467; A61B 17/0483; A61B 17/0485; A61B 2017/0474; A61B 2017/0496
See application file for complete search history.

(56) References Cited

U.S. PATENT DOCUMENTS 5,133,723 A *  7/1992  Li .................... A61B 17/0469
                                                            289/17
5,176,691 A *  1/1993  Pierce ............ A61B 17/0469
                                                            606/144
(Continued)

FOREIGN PATENT DOCUMENTS

CN    101953703 A    1/2011
CN    102046096 A    5/2011
(Continued)

OTHER PUBLICATIONS

International Search Report and Written Opinion for International Patent Application No. PCT/US2017/050647, dated Dec. 4, 2017.
(Continued)

*Primary Examiner* — Ryan J. Severson
(74) *Attorney, Agent, or Firm* — Dergosits & Noah LLP; Todd A. Noah (57) ABSTRACT

Excess suture material may be trimmed after knot tying using a device having an elongated shaft, an elongated tubular cutter disposed over the shaft and an elongated tubular barrel disposed over the cutter. A suture loader at a distal end of the shaft that engages suture material may be opened and closed by a first actuator that causes relative motion between the shaft and the barrel. A second actuator may cause relative motion between the cutter and both of the barrel and the shaft to sever suture material engaged by the closed suture loader.

21 Claims, 7 Drawing Sheets

(52) U.S. Cl.
CPC .... *A61B 17/06166* (2013.01); *A61B 17/0483* (2013.01); *A61B 2017/0474* (2013.01); *A61B 2017/0488* (2013.01); *A61B 2017/0496* (2013.01)

(56) References Cited

U.S. PATENT DOCUMENTS

| | | | | |
|---|---|---|---|---|
| 5,423,837 | A * | 6/1995 | Mericle | A61B 17/0469 606/148 |
| 5,520,702 | A * | 5/1996 | Sauer | A61B 17/0469 29/751 |
| 5,755,730 | A * | 5/1998 | Swain | A61B 17/0467 606/148 |
| 6,254,620 | B1 * | 7/2001 | Koh | A61B 17/0467 30/278 |
| 6,733,509 | B2 * | 5/2004 | Nobles | A61B 17/0467 606/138 |
| 6,866,673 | B2 * | 3/2005 | Oren | A61B 17/0483 289/17 |
| 7,094,246 | B2 * | 8/2006 | Anderson | A61B 17/0485 606/139 |
| 7,491,212 | B2 * | 2/2009 | Sikora | A61B 17/0467 606/148 |
| 7,879,055 | B1 * | 2/2011 | Stone | A61B 17/0482 606/170 |
| 7,918,867 | B2 * | 4/2011 | Dana | A61B 17/0467 606/144 |
| 7,992,571 | B2 * | 8/2011 | Gross | A61B 17/0485 128/898 |
| 8,105,355 | B2 * | 1/2012 | Page | A61B 17/0485 606/232 |
| 8,211,123 | B2 * | 7/2012 | Gross | A61B 17/0485 606/148 |
| 8,252,005 | B2 * | 8/2012 | Findlay, III | A61B 17/0487 606/139 |
| 8,425,555 | B2 * | 4/2013 | Page | A61B 17/0485 606/232 |
| 8,585,720 | B2 * | 11/2013 | Gross | A61B 17/0485 606/148 |
| 8,603,125 | B2 * | 12/2013 | Stone | A61B 17/0469 606/170 |
| 8,834,497 | B2 * | 9/2014 | Snell | A61B 17/0467 606/148 |
| 8,911,457 | B2 * | 12/2014 | Koogle, Jr. | A61B 17/0467 606/148 |
| 8,911,461 | B2 * | 12/2014 | Traynor | A61B 17/0467 606/170 |
| 8,939,998 | B2 * | 1/2015 | Miyamoto | A61B 17/0487 606/144 |
| 9,247,935 | B2 * | 2/2016 | George | A61B 17/0467 |
| 9,332,980 | B2 * | 5/2016 | George | A61B 17/0469 |
| 9,642,615 | B2 * | 5/2017 | Halac | A61B 17/0487 |
| 9,750,494 | B2 * | 9/2017 | Gross | A61B 17/0467 |
| 10,143,464 | B2 * | 12/2018 | George | A61B 17/0467 |
| 10,426,462 | B2 * | 10/2019 | Haberman | A61B 17/0467 |
| 10,507,019 | B2 * | 12/2019 | Gross | A61B 17/0467 |
| 2002/0087178 | A1 * | 7/2002 | Nobles | A61B 17/0467 606/167 |
| 2003/0181926 | A1 * | 9/2003 | Dana | A61B 17/0485 606/148 |
| 2004/0097865 | A1 | 5/2004 | Anderson et al. | |
| 2004/0122450 | A1 * | 6/2004 | Oren | A61B 17/0483 606/148 |
| 2004/0162569 | A1 * | 8/2004 | Sikora | A61B 17/0483 606/148 |
| 2004/0210238 | A1 * | 10/2004 | Nobles | A61B 17/0467 606/114 |
| 2004/0249393 | A1 * | 12/2004 | Weisel | A61B 17/06109 606/144 |
| 2006/0047314 | A1 * | 3/2006 | Green | A61B 17/0487 606/232 |
| 2006/0069397 | A1 | 3/2006 | Nobles et al. | |
| 2006/0069399 | A1 * | 3/2006 | Weisel | A61B 17/0469 606/148 |
| 2007/0005081 | A1 * | 1/2007 | Findlay, III | A61B 17/0467 606/148 |
| 2007/0173865 | A1 * | 7/2007 | Oren | A61B 17/0467 606/148 |
| 2008/0051837 | A1 | 2/2008 | To et al. | |
| 2008/0234729 | A1 * | 9/2008 | Page | A61B 17/0485 606/232 |
| 2009/0272783 | A1 | 11/2009 | Crainich et al. | |
| 2010/0049218 | A1 * | 2/2010 | Miyamoto | A61B 17/12013 606/144 |
| 2010/0211053 | A1 | 8/2010 | Ross et al. | |
| 2011/0100173 | A1 * | 5/2011 | Stone | A61B 17/0482 83/13 |
| 2012/0089182 | A1 * | 4/2012 | Page | A61B 17/0487 606/232 |
| 2013/0072949 | A1 | 3/2013 | Halac et al. | |
| 2014/0005689 | A1 | 1/2014 | Griffiths | |
| 2015/0088163 | A1 * | 3/2015 | George | A61B 17/0467 606/138 |
| 2015/0142022 | A1 * | 5/2015 | George | A61B 17/0469 606/148 |
| 2019/0374215 | A1 * | 12/2019 | Juan | A61B 17/0469 |

FOREIGN PATENT DOCUMENTS

| | | |
|---|---|---|
| EP | 1847226 | 10/2007 |
| EP | 2029031 A2 | 3/2009 |
| JP | 2005-066100 A | 3/2005 |
| JP | 2006-503595 A | 2/2006 |
| JP | 2008-514305 A | 5/2008 |
| WO | 2003059174 | 7/2003 |

OTHER PUBLICATIONS

First Office Action from corresponding Chinese Patent Application No. 201780069449.5, dated Jun. 15, 2021.

Search Report from corresponding Japanese Patent Application No. 2019-513886, dated Jul. 8, 2021.

* cited by examiner

SYSTEM AND METHOD FOR SUTURE TRIMMING

RELATED APPLICATIONS

This application claims the benefit of U.S. Provisional Patent Application No. 62/385,436, filed Sep. 9, 2016, the contents of which is incorporated by reference in its entirety.

FIELD OF THE PRESENT DISCLOSURE

The present disclosure relates generally to devices and methods for use in trimming suture material. In particular, techniques are disclosed for suture trimming that may be used to close a puncture or opening associated with a percutaneous surgery.

BACKGROUND

Techniques have been developed to allow an increasing number and variety of procedures to be performed percutaneously as minimally invasive alternatives to conventional "open" surgeries. Such techniques provide the benefits of reducing post-operative pain, decreasing hospital stays and periods of disability, and lowering costs for both hospitals and patients. Generally, these procedures utilize one or more elongated instruments that are introduced through a patient's skin for use in carrying out the procedure, which may include clinical treatments such as percutaneous coronary intervention. As an illustration, the physician may gain vascular access through introducer and introducer sheath to deliver diagnostic or therapeutic device(s) into vessel percutaneously without cutting down the skin and subcutaneous tissue in a percutaneous coronary intervention. Correspondingly, it is desirable to attempt repair the access site or otherwise provide support for the surrounding tissue during the post-operative healing process.

Notably, closing the openings formed to carry out the percutaneous procedure with sutures may reduce recovery time, minimize the risk of infection or provide other benefits. In clinical practices, manual compression and vascular closure devices are standard procedures to achieve hemostasis after interventions. The principle of manual compression is to apply external compression force upon an adjacent area upstream of the access site for a certain period of time to reduce blood flow and control bleeding. However, this is time-consuming, inconvenient, and uncomfortable for the patient. Although other methods of closing wounds have been developed, including the use of staples and clips, suturing remains a beneficial technique that provides advantages over these alternatives. Specifically, suture-based technologies have been developed to improve efficiency and safety of hemostasis. Such suture-based closure devices allow the physician to place, anchor suture(s) around a vessel opening percutaneously, and close the access site after the procedure by forming sliding knot(s) that may be cinched to draw the opening closed. After the knots are delivered and hemostasis is achieved, the excess length of sutures should be trimmed and removed appropriately. As will be described in the materials below, the systems and methods of this disclosure satisfy these and other needs.

SUMMARY

This disclosure includes a device for trimming suture material, including an elongated shaft, an elongated tubular cutter disposed over the shaft, an elongated tubular barrel disposed over the cutter and a suture loader at a distal end of the shaft configured to engage suture material. A first actuator may be configured to cause relative motion between the shaft and the barrel and a second actuator may be configured to cause relative motion between the cutter and both of the barrel and the shaft.

In one aspect, the suture loader comprises a head at the distal end of the shaft and a longitudinal groove formed in the head and sized to receive the suture material. The suture loader may have a gap in the shaft proximal to the head. The suture loader may also have a hook extending into the gap and aligned with an edge of the groove.

In one aspect, the device may include an opening at the distal end of the barrel that is configured to allow suture material to extend from the suture loader when the shaft and the barrel are in a closed position.

In one aspect, a distal portion of the shaft may have a surface formed by a change in shaft diameter against which the cutter contacts when the cutter is moved distally with respect to the shaft.

In one aspect, a distal portion of the shaft may have a knot advancing surface.

In one aspect, the first actuator may be a slider such that motion of the slider in a distal direction corresponds to a relative change in position between the shaft and the barrel to expose a distal end of the shaft having the suture loader. The first actuator may require disengagement through motion in a different direction before allowing the motion in the distal direction.

In one aspect, the first actuator may be a depressible button such that inward pressure on the button corresponds to a relative change in position between the shaft and the barrel to expose a distal end of the shaft having the suture loader. The inward pressure may be translated to a longitudinal motion by cooperating ramps coupled to the first actuator.

In one aspect, the second actuator may be a lever such that motion of an end of the lever corresponds to a distal motion of the cutter. Proximal motion of the end of the lever may correspond to a distal motion of the cutter.

In one aspect, a proximal end of the shaft may be coupled to and be moveable with respect to the barrel by the first actuator and a proximal end of the cutter may be coupled to and be moveable with respect to the barrel by the second actuator.

In one aspect, a proximal portion of the barrel may be coupled to and be moveable with respect to the shaft by the first actuator and a proximal end of the cutter may be coupled to and be moveable with respect to the shaft by the second actuator.

This disclosure also includes a method for trimming excess suture material after knot tying. The method may involve providing suture trimming device having an elongated shaft, an elongated tubular cutter disposed over the shaft, and an elongated tubular barrel disposed over the cutter, opening a suture loader by causing relative motion between the barrel and the shaft using a first actuator, engaging excess suture material extending from a preformed knot with the suture loader, closing the suture loader around the excess suture material as a result of relative motion between the barrel and the shaft and operating a second actuator to cause the cutter to advance distally to sever the engaged excess suture material.

In one aspect, engaging the excess suture material may longitudinally stabilize the suture material.

In one aspect, a surface of a distal end of the shaft may be advanced against the preformed knot. The preformed knot may be cinched against the surface. Alternatively or in addition, advancing the surface of the distal end of the shaft may position the preformed knot at a desired location.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. It should be appreciated that the techniques of this disclosure may be applied in conjunction with any procedure involving the placing of a suture knot within the interior of a patient's body.

Finally, as used in this specification and the appended claims, the singular forms "a, "an" and "the" include plural referents unless the content clearly dictates otherwise.

Figure 1:
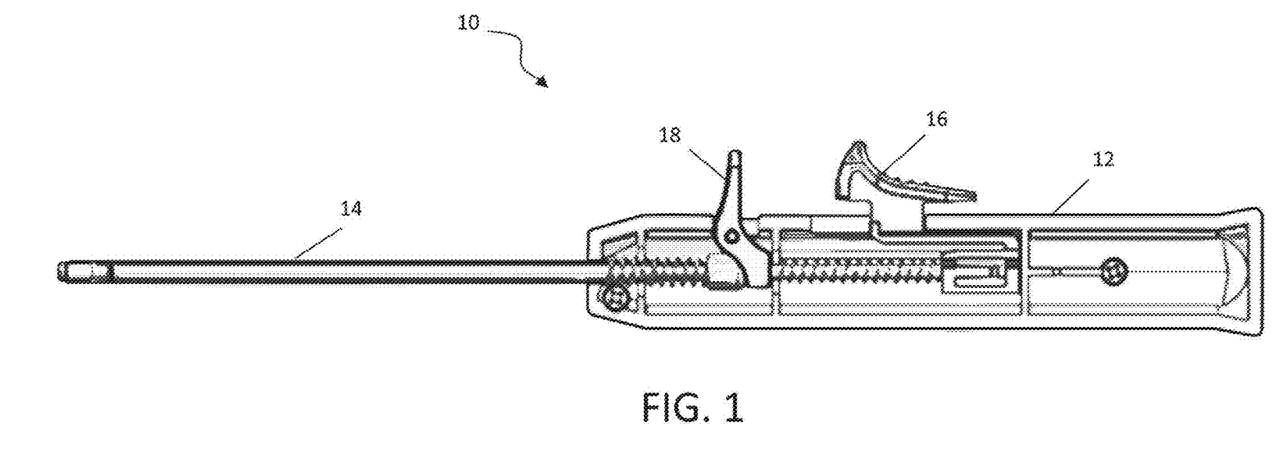
FIG. 1 depicts a schematic view of an embodiment of a suture trimming device.

Referring to FIG. 1, a suture trimming device 10 according to one embodiment is shown, partially in section, that is adapted to remove the excess suture material from knotted tissue percutaneously. Functionality associated with suture trimming device 10 includes loading suture material into the device and cutting the excess free at a desired location adjacent the formed knot. As illustrated, suture trimmer 10 includes handle 12 to facilitate manipulation by a physician and elongated suture cutting assembly 14. Associated with handle 12 are first actuator 16 and second actuator 18 that may be used to selectively move components of suture cutting assembly 14 when performing the suture loading and trimming operations.

Figure 2:
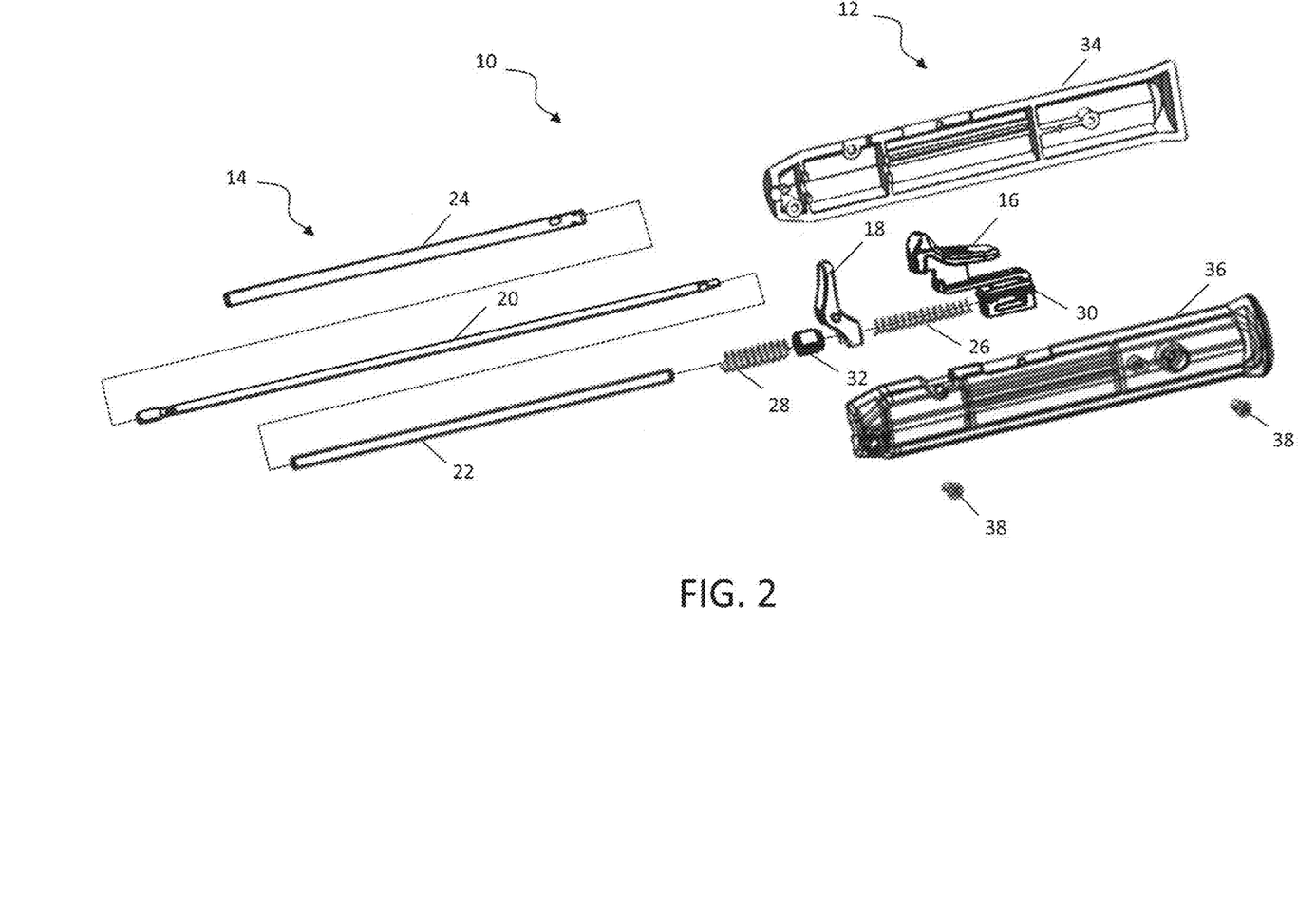
FIG. 2 schematically depicts an exploded view of an embodiment of a suture trimming device.

Further details of suture trimming device 10 are shown in the exploded view of FIG. 2. Suture cutting assembly 14 includes shaft 20, cutter 22, and barrel 24 coaxially disposed within each other. In this embodiment, shaft 20 when positioned within barrel 24 forms an annular, coaxial lumen through which cutter 22 may travel. As will be described below, shaft 20 may be selectively moved with respect to barrel 24 during a suture loading operation under control of first actuator 16, while cutter 22 may be selectively moved with respect to shaft 20 and barrel 24 during a suture cutting operation under control of second actuator 18. The distal ends of shaft 20 and barrel 24 cooperate to form a suture loader, that may be opened and closed by relative motion between shaft 20 and barrel 24. A proximal end of shaft 20 may be coupled to first actuator 16, such that shaft 20 is biased in a proximal direction by first spring member 26. A proximal end of cutter 22 may be coupled to second actuator 18 by link 32, such that cutter 22 is biased in a proximal direction by second spring member 28. Shaft 20 and cutter 22 may be independently slidable within barrel 24 in this embodiment, although other embodiments may involve a static shaft, with a moveable barrel and cutter as exemplified by FIG. 12, discussed below. The proximal end of shaft 20 may be coupled to first actuator 16 by link 30, while the proximal end of cutter 22 may be coupled to second actuator 18 by link 32. Handle 12 may be formed from opposing housing portions 34 and 36 and secured together by screws 38.

Figure 3:
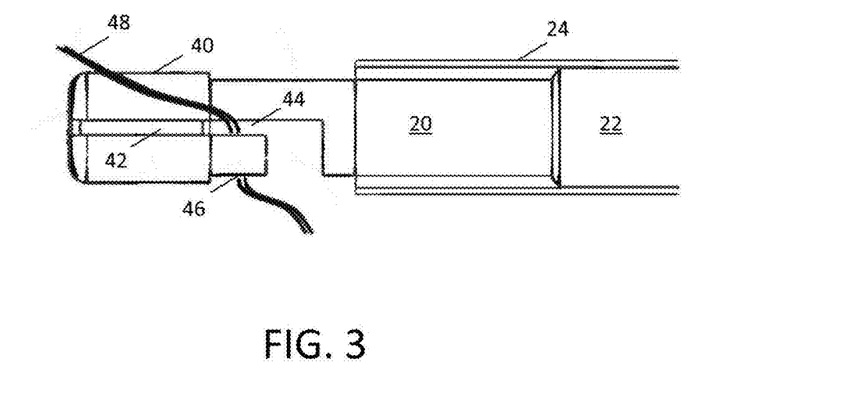
FIG. 3 schematically depicts an embodiment of a distal end of a suture trimming device with an open suture loader.
Figure 4:
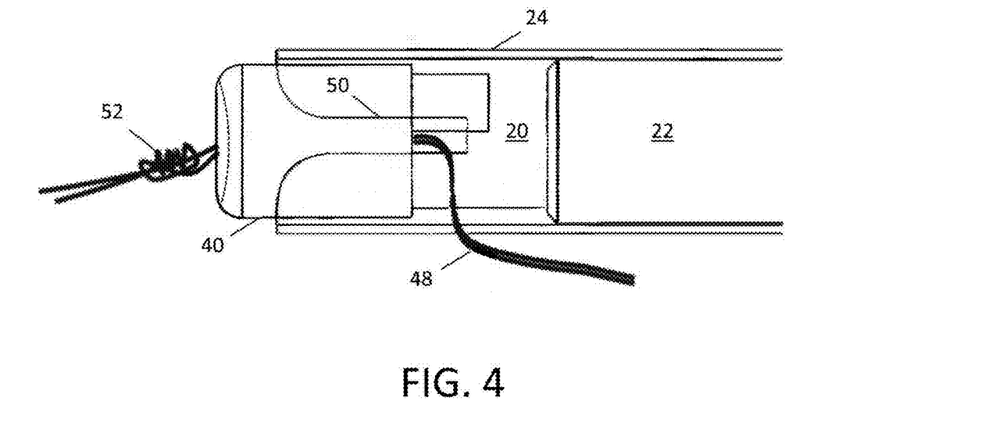
FIGS. 4 and 5 schematically depict opposing views of an embodiment of a distal end of a suture trimming device with a closed suture loader.
Figure 5:
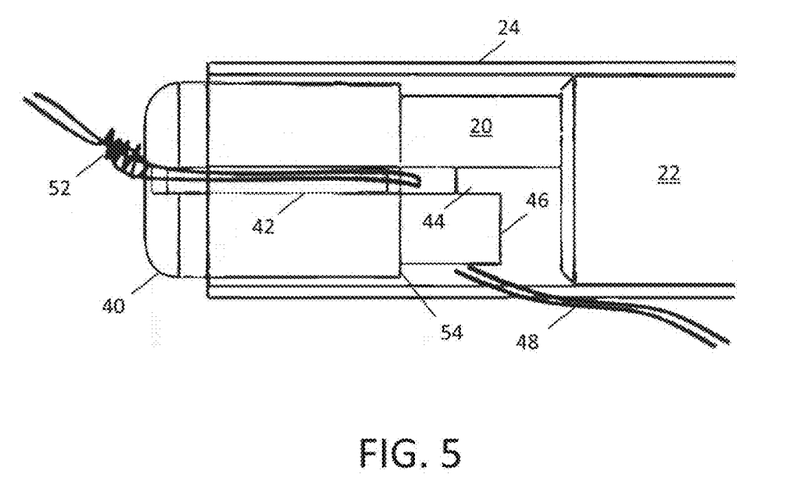

To help illustrate operations involving the loading of suture into suture trimming device 10, FIGS. 3-5 show detail views of the distal end of suture cutting assembly 14 and the selective positioning of shaft 20 in relation to barrel 24 as may be controlled through first actuator 16. In FIG. 3, shaft 20 is in a more distal position relative to barrel 24 as controlled by first actuator 16 (not shown in this view) as will be discussed below. In this distal position, the end of shaft 20 protrudes from barrel 24, forming an open suture loader that includes head 40 of shaft 20, with a longitudinally oriented groove 42 sized to accept the suture. Proximal to the head 40 is gap 44, such that hook 46, aligned with one edge of groove 42, is configured to capture suture 48 as indicated. For example, gap 44 may be positioned over suture 48 to allow it to be engaged by hook 46 with the distally extending portion of suture 48 able to be disposed within groove 42. In this open position of the suture loader, at least a portion of gap 44 is exposed beyond the distal end of barrel 24. As indicated, cutter 22 remains in a relatively proximal position during the suture loading operation. Other suitable mechanisms may be employed to load suture material into a distal portion of shaft 20 as desired.

Next, FIG. 4 shows the distal end of suture cutting assembly 14 including the suture loader from the opposite side, with the distal end of shaft 20 in a more proximal position relative to barrel 24, corresponding to the suture loader being in a closed position. As may be seen, when shaft 20 is in this position, the suture loader is effectively closed around suture 48. Specifically, at least a portion of head 40 has been pulled within the distal end of barrel 24. Suture 48 lies within groove 42, allowing head 40 to fit within barrel 24. As such, the closed position is characterized by the distal end of barrel 24 extending past gap 44. The proximal extension of suture 48 travels from gap 44 out opening 50 formed in barrel 24, which may be configured as a longitudinal slot and may be sized appropriately, such as by having dimensions to accommodate the two strands of suture 48. Tension may then be applied to the proximal end of suture 48 in order to bring knot 52 into proximity of the surface of head 40. Groove 42 may be sized to resist entry of knot 52 so that the physician may readily determine when knot 52 abuts head 40. Moreover, since knot 52 may be too large to fit within groove 42, the distal end of head 40 may form a knot advancing surface. As will be appreciated, this may be used by the physician to aid in placing the knot at a desired location and/or when cinching the suture material to tighten the knot. For example, groove 42 may serve to limit suture movement and stabilize interaction between suture 48 and device 10 as it is being advanced over the suture 48 following the loading operation. Optionally, to help ensure stability while device 10 is in contact with knot 52, the distal surface of head 40 may be recessed radially inward to receive the knot 52, forming a concave surface indicated by the dashed line. Thus, knot 52 may be steadied by device 10 as it is being advanced to a desired location or being tightened as indicated above. Correspondingly, the knot advancing surface may be used to perform one or more aspects associated with suturing, including completing a preformed knot, positioning a preformed knot and/or tightening a preformed knot.

Further, FIG. 5 shows the distal end of suture cutting assembly 14 with the suture loader still in the closed position from the original side depicted in FIG. 3. To aid visualization of the cooperation between the various components of suture trimming device 10, barrel 24 is depicted as being transparent in these figures, but in practice may be formed from any suitable biocompatible material including metals or polymers. Accordingly, in the view of FIG. 5, which as with FIG. 4 depicts shaft 20 in a proximal position relative to barrel 24, it may be seen that knot 52 has been drawn into contact with head 40, so that the proximally extending portion of suture 48 lies within groove 42, is engaged by hook 46 and travels through gap 44 out opening 50 (not visible in this view) of barrel 24.

Figure 6:
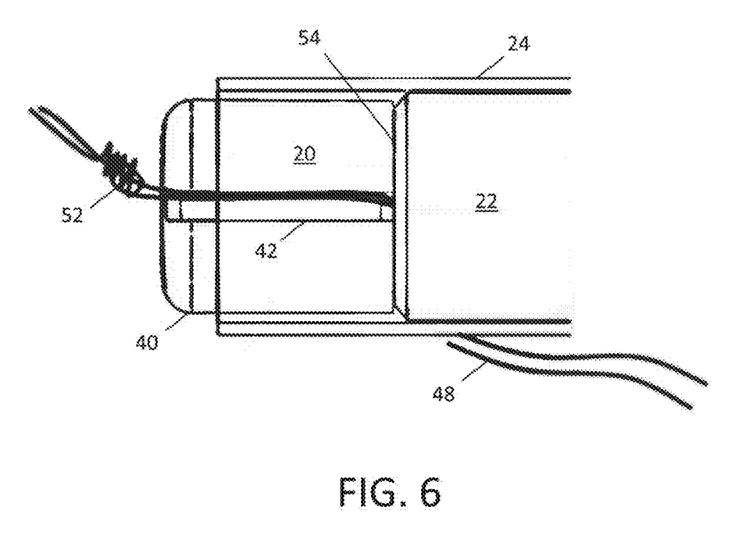
FIG. 6 schematically depicts an embodiment of a distal end of a suture trimming device with a closed suture loader after cutting excess suture material.

With shaft 20 in its proximal position relative to barrel 24 causing the suture loader to be in the closed position, suture 48 may be cut by advancing cutter 24 distally with respect to shaft 20 and barrel 24, for example, by appropriate manipulation of second actuator 18 (not shown in this view) as discussed below. Cutter 22 is depicted in FIG. 6 in its distal position and suture 48 has been trimmed. As will be appreciated, the coaxial relationship of cutter 22 within barrel 24 and disposed over shaft 20 ensures that cutter 22 engages suture 48 where it travels from groove 42 into gap 44. The distal end of cutter 22 may have a beveled, sharpened edge in order to more easily sever the suture material. As desired, head 40 may have a surface such as flange 54 against which the sharpened edge of cutter 22 mates to facilitate the trimming of suture 48. Flange 54 may be formed by a change in diameter of shaft 20 or other suitable means. Thus, when knot 52 abuts head 40 at the opening of groove 42, a consistent length of suture material extends through groove 42 to gap 44 where cutter 22 engages it, ensuring the trimming operation leaves sufficient material. The amount of suture material left during the trimming operation may be established by the size of head 40 chosen and therefore the length of groove 42.

Figure 7:
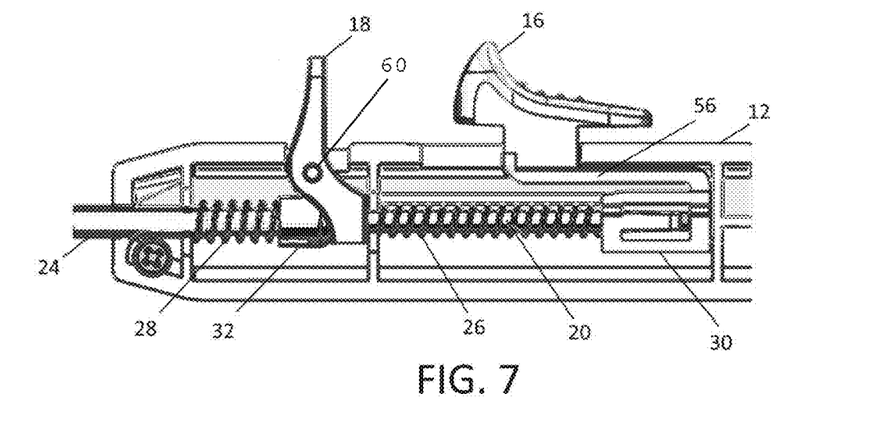
FIGS. 7-9 schematically depict operations involving an embodiment of a first actuator of a suture trimming device.
Figure 8:
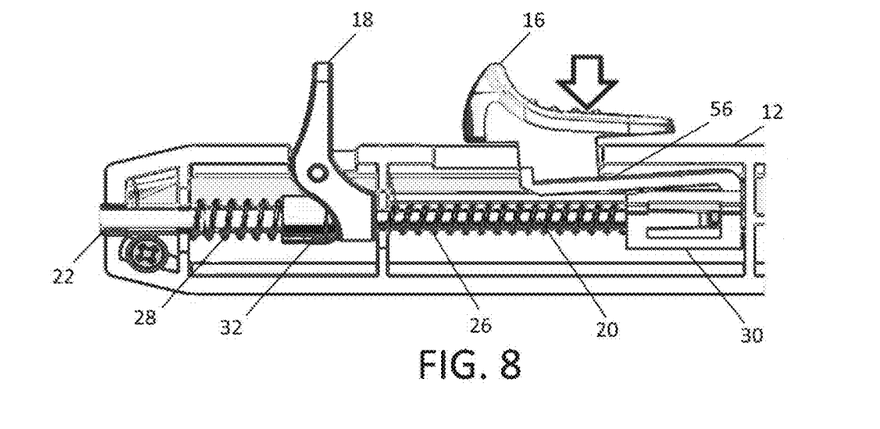
Figure 9:
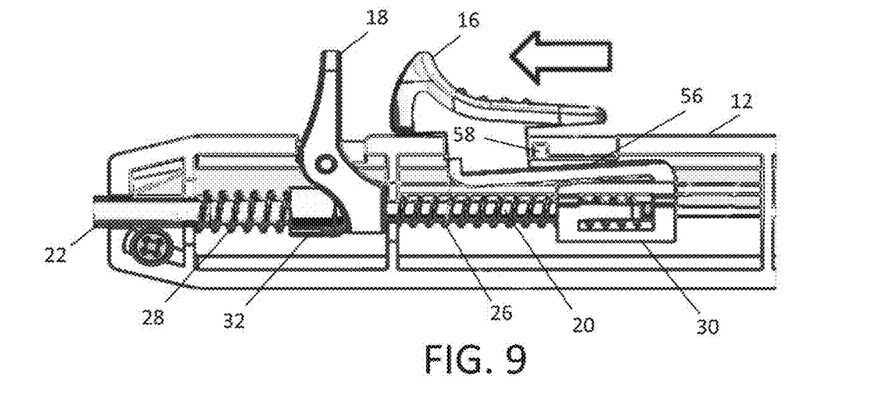

Turning now to FIGS. 7-9, additional details regarding first actuator 16 and second actuator 18 are illustrated. In particular, the sequence of FIGS. 7-9 show operations involving movement of first actuator 16 in a first direction perpendicular to the longitudinal axis of handle 12 to release locking member 56, followed by a distal movement in a second direction, parallel with the longitudinal axis. For example, FIG. 7 shows first actuator 16 in its nominal, proximal position, corresponding to the related closed suture loader position with shaft 20 in a proximal position with respect to barrel 24 (not shown in this view). As noted above, the proximal end of shaft 20 is coupled to first actuator 16 by link 30 and is biased in the proximal direction by spring member 26. Locking member 56 may be made from a resilient material and nominally may engage recess 58 (not visible in this view, but shown in FIG. 9) formed in at least one of the housings of handle 12, such as portion 34 or 36. Correspondingly, an application of force to actuator 16 in an inward, perpendicular direction as indicated by the arrow in FIG. 8 deflects and disengages locking member 56. Then, first actuator 16 may be slid distally by applying force in the longitudinal direction indicated by the arrow in FIG. 9, compressing spring member 26 and driving shaft 20 distally through translation of link 30. At the distal range of travel for first actuator 16, shaft 20 may be in a distal position with respect to barrel 24, corresponding to the open suture loader position depicted in FIG. 3. After suture 48 has been loaded through groove 42, gap 44 and engaged by hook 46 as described above, first actuator 16 may be returned to the position shown in FIG. 7 by removing the distally oriented force, thereby allowing spring member 26 to expand from its compressed state, pushing link 30 and correspondingly shaft 20 back to the proximal position associated with a closed suture loader. Alternatively or in addition, the physician may manually apply a proximal sliding force to first actuator 16 to achieve the same result. Due to the resilient nature of locking member 56, it re-engages recess 58, to retain shaft 20 in the closed position.

Correspondingly, once suture 48 has been loaded and first actuator 16 returned to its locked, proximal position, second actuator 18 may be manipulated to effect the cutting operation. In this embodiment, second actuator 18 is configured as a lever, pivoting around axle 60. As such, applying a proximally-oriented force to second actuator 18 drives link 32 distally, compressing spring member 28. Since the proximal end of cutter 22 is coupled by link 32, it is advanced relative to shaft 20 and barrel 24 as described above. Since locking member 56 retains shaft 20 in its more proximal position, the sharpened distal edge of cutter 22 is driven against flange 54 to sever the suture material caught between these elements. Removal of the proximally-oriented force from second actuator 18 allows compressed spring member 28 to expand, withdrawing cutter 22 to its nominal, proximal position after the cutting operation is performed. Alternatively or in addition, the physician may manually apply a distal force to second actuator 18 to achieve the same result.

Figure 10:
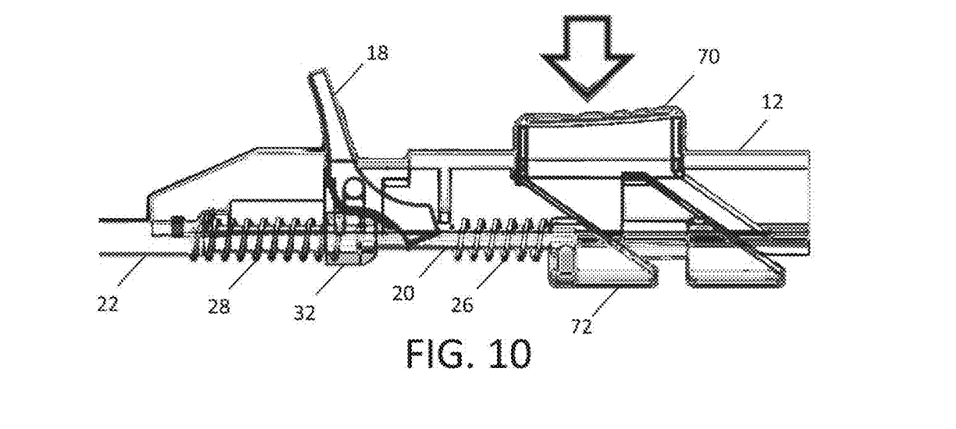
FIGS. 10 and 11 schematically depict operations involving another embodiment of a first actuator of a suture trimming device.
Figure 11:
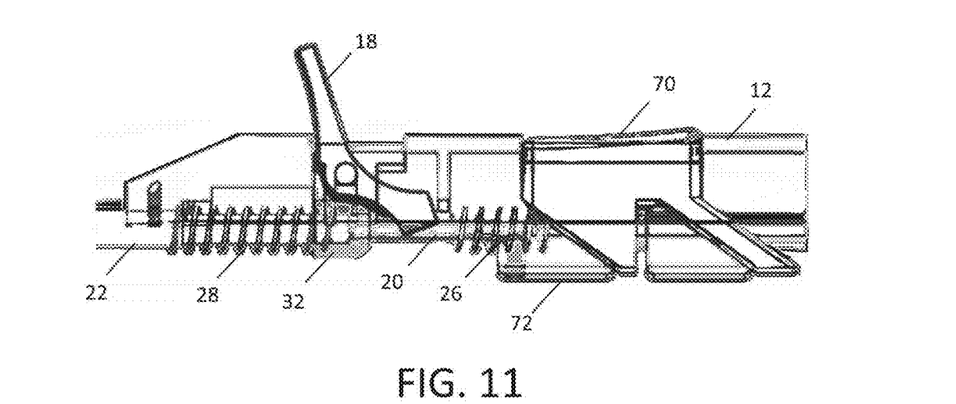

It should be appreciated that the specific mechanisms described above with respect to first actuator 16 and second actuator 18 are intended as examples only and that any suitable means of causing relative motion of shaft 20 and/or cutter 22 with respect to barrel 24 may be employed. To help illustrate, an alternative embodiment is depicted in FIGS. 10 and 11 that features first actuator 70 configured as a depressible button as compared to the sliding mechanism of first actuator 16. In these illustrations, similar elements having similar functions to those described above have been given the same reference numbers. For example, the components associated with second actuator 18 are generally similar and may perform the operations as described above. Further, shaft 20 may be biased proximally by spring member 26 in a similar manner to the above embodiment. The proximal end of shaft 20 is coupled to first actuator 70 by link 72 as shown. First actuator 70 and link 72 cooperate through opposing ramps to translate a force applied perpendicularly to handle 12 into a longitudinal translation of shaft 20. For example, in the nominal closed position, spring member 26 biases shaft 20 proximally in a similar manner to that described above, with first actuator 70 in a first, non-depressed position. By applying an inward force as indicated by the arrow, first actuator 70 may be depressed into the second position shown in FIG. 11. The inclined faces of the ramps of link 72 and first actuator 70 slide with respect to each other, translating the inward, perpendicular motion of first actuator 70 into a distal motion of link 72, which in turn compresses spring member 26 and drives shaft 20 distally, opening the suture loader. After loading the suture material as described above, the inward force applied to first actuator 70 may be withdrawn, so that expansion of spring member 26 pushes link 72, along with shaft 20, proximally and closes the suture loader. Interaction of the ramped surfaces of first actuator 70 and link 72 cause first actuator to assume its initial, non-depressed position. Second actuator 18 may then be manipulated to advance cutter 22 and trim the captured suture material.

Figure 12:
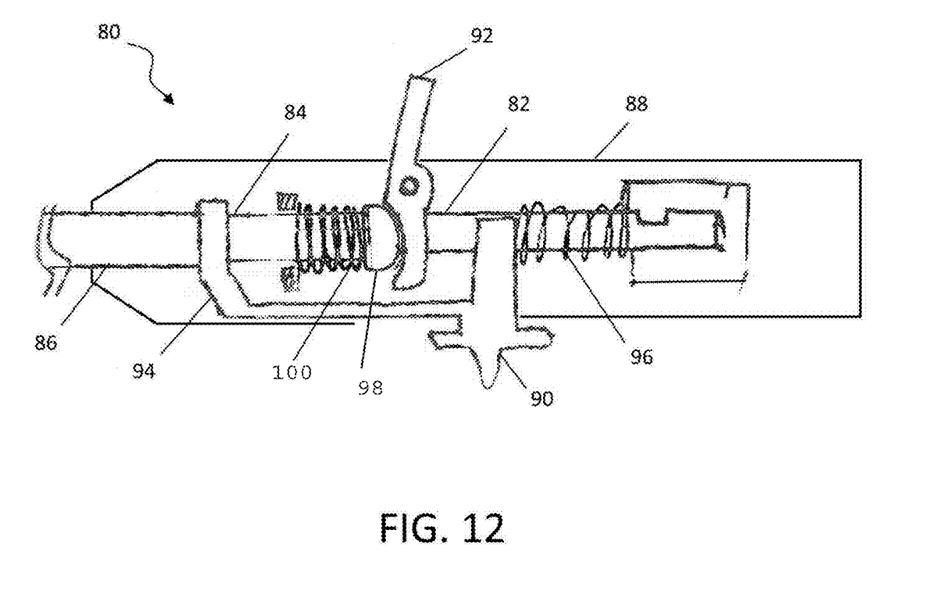
FIG. 12 depicts a schematic view of another embodiment of a suture trimming device.

The techniques of this disclosure may also be extended to other suture trimmer configurations. For example, the embodiments discussed above involve a static barrel, with shaft and cutter elements that move in relation. However, with suitable modifications, the suture trimmer device may have a shaft that remains static and barrel and cutter elements that move. To help illustrate, FIG. 12 depicts an embodiment of suture trimming device 80 exemplifying these characteristics. Suture trimming device 80 also has an elongated suture cutting assembly with a shaft 82 coaxially disposed within a tubular cutter 84 and an outer barrel 86. These elements are similar to the above embodiment particularly with regard to the suture loader aspects of the distal end shaft 82, which may be configured to capture and engage suture material, as well as the distal end of cutter 84, which may be configured to trim suture material, both as described above. However, in this embodiment, shaft 82 remains fixed, while barrel 86 may be moved proximally to expose the distal end of shaft 82 and open the suture loader or moved distally to close the suture loader so that excess suture material may be trimmed. Cutter 84 is able to slide over shaft 82 independently of barrel 86. As illustrated, suture trimmer 80 includes handle 88 with first actuator 90 and second actuator 92 that may be used to selectively move barrel 86 and cutter 84, respectively. A proximal portion of barrel 86 may be coupled to first actuator 90 by link 94, such that barrel 86 is biased in a distal direction by first spring member 96. Further, a proximal end of cutter 84 may be coupled to second actuator 92 by link 98, such that cutter 84 is biased in a proximal direction by second spring member 100.

Suture trimming device 80 may be used in a similar manner to the other embodiments of this disclosure to remove excess suture material. As discussed, barrel 86 is biased in a distal direction to place the suture loader in a closed position. Accordingly, the physician may employ first actuator 90 to expose the distal end of shaft 82 to open the suture loader when loading the suture material. By sliding first actuator 90 proximally, link 94 pulls barrel 86 proximally, so that the distal end of shaft 82 protrudes. Once the suture material is captured, using the shaft head elements including a groove, a gap and a hook as described above, first actuator 90 may then be released (and/or manually returned to its more distal position) to extend barrel 86 over the captured suture material, closing the suture loader. Second actuator 92 is configured similarly to actuator 18 and performs a similar function. The physician applies a proximal force to the end of second actuator 92, causing it to pivot and drive cutter 84 distally, compressing second spring member 98 and severing the excess suture material engaged by the suture loader. As with the other embodiments, the first and/or second actuator may rely on different mechanics to achieve the desired relative motion between shaft 82, cutter 84 and barrel 86.

Described herein are certain exemplary embodiments. However, one skilled in the art that pertains to the present embodiments will understand that the principles of this disclosure can be extended easily with appropriate modifications to other applications.

What is claimed is:

1. A device for trimming suture material comprising an elongated shaft, an elongated tubular cutter disposed over the shaft having a circumferential cutting edge, an elongated tubular barrel disposed over the cutter, a suture loader at a distal end of the shaft configured to engage suture material, a first actuator configured to cause relative distal translational motion of the shaft with respect to the barrel and a second actuator configured to cause relative translational motion between the cutter and both of the barrel and the shaft.

2. The device of claim 1, wherein the suture loader comprises a head at the distal end of the shaft and a longitudinal groove formed in the head and sized to receive the suture material.

3. The device of claim 2, wherein the suture loader further comprises a gap in the shaft proximal to the head.

4. The device of claim 3, wherein the suture loader further comprises a hook extending into the gap and aligned with an edge of the groove.

5. The device of claim 1, further comprising an opening at the distal end of the barrel that is configured to allow suture material to extend from the suture loader when the shaft and the barrel are in a closed position.

6. The device of claim 1, wherein a distal portion of the shaft has a surface formed by a change in shaft diameter against which the cutter contacts when the cutter is moved distally with respect to the shaft.

7. The device of claim 1, wherein a distal portion of the shaft has a knot advancing surface.

8. The device of claim 1, wherein the first actuator comprises a slider such that motion of the slider in a distal direction corresponds to a relative change in position between the shaft and the barrel to expose a distal end of the shaft having the suture loader.

9. The device of claim 8, wherein the first actuator requires disengagement through motion in a different direction before allowing the motion in the distal direction.

10. The device of claim 1, wherein the first actuator comprises a depressible button such that inward pressure on the button corresponds to a relative change in position between the shaft and the barrel to expose a distal end of the shaft having the suture loader.

11. The device of claim 10, wherein the inward pressure is translated to a longitudinal motion by cooperating ramps coupled to the first actuator.

12. The device of claim 1, wherein the second actuator comprises a lever such that motion of an end of the lever corresponds to a distal motion of the cutter.

13. The device of claim 12, wherein proximal motion of the end of the lever corresponds to a distal motion of the cutter.

14. The device of claim 1, wherein a proximal end of the shaft is coupled to and is moveable with respect to the barrel by the first actuator and a proximal end of the cutter is coupled to and is moveable with respect to the barrel by the second actuator.

15. The device of claim 1, wherein a proximal end of the barrel is coupled to and is moveable with respect to the shaft by the first actuator and a proximal end of the cutter is coupled to and is moveable with respect to the shaft by the second actuator.

16. A method for trimming excess suture material after knot tying comprising:

providing a suture trimming device having an elongated shaft, an elongated tubular cutter disposed over the shaft with a circumferential cutting edge, and an elongated tubular barrel disposed over the cutter;

opening a suture loader by causing relative distal translational motion of the shaft with respect to the barrel using a first actuator;

engaging excess suture material extending from a preformed knot with the suture loader;

closing the suture loader around the excess suture material as a result of relative motion between the barrel and the shaft; and operating a second actuator to cause the cutter to advance distally to sever the engaged excess suture material.

17. The method of claim 16, wherein engaging the excess suture material longitudinally stabilizes the suture material.

18. The method of claim 16, further comprising advancing a surface of a distal end of the shaft against the preformed knot.

19. The method of claim 18, further comprising cinching the preformed knot against the surface.

20. The method of claim 18, wherein advancing the surface of the distal end of the shaft positions the preformed knot at a desired location.

21. The method of claim 16, wherein a distal portion of the shaft has a surface formed by a change in shaft diameter against which the cutter contacts when the cutter is moved distally with respect to the shaft.

* * * * *